United States Patent [19]

Goedemans

[11] 4,360,509

[45] Nov. 23, 1982

[54] VIVO RADIOASSAY PROCESS

[75] Inventor: Wilhelmus T. Goedemans, Schoorl, Netherlands

[73] Assignee: Byk-Mallinckrodt CIL B.V., Netherlands

[21] Appl. No.: 105,202

[22] Filed: Dec. 19, 1979

[51] Int. Cl.$^3$ ............................ A61K 49/00; A61K 43/00
[52] U.S. Cl. ............................................ 424/1; 424/9
[58] Field of Search .......................................... 424/1, 9

[56] References Cited

U.S. PATENT DOCUMENTS 4,017,596  4/1977  Loberg et al. ............................ 424/1

OTHER PUBLICATIONS

Heindel et al., Ed., The Chemistry of Radiopharmaceuticals, Masson Publishing USA, Inc., New York (1978), p. 43.

Merrick et al., from Medical Radioisotope Scintigraphy 1972, IAGA, Vienna, 1973, pp. 721–729.

Primary Examiner—Christine M. Nucker
Attorney, Agent, or Firm—Bernard, Rothwell & Brown

[57] ABSTRACT

There is disclosed an in vivo radioassay process in which a radioactive chelate of indium and an 8-hydroxyquinoline is introduced into a warmblooded animal having an inflammatory reaction in an area in which the chelate would not accumulate to the same extent if the inflammation were not present. The chelate gathers in the inflamed area, for instance, in a body abscess, or other injury, and its location is determined by radio surveying the body by an external imaging technique.

7 Claims, No Drawings

VIVO RADIOASSAY PROCESS

It is highly desirable to determine the location of inflammatory reactions in warmblooded animals without having to invade the body by surgery or introduction of a mechanical device into the body in the area of the inflammation which is often painful to the patient and whose proper utilization may require a great deal of skill. The present invention is directed to a process in which an inflammatory reaction, for instance, an abscess or other injury, can be located in the body without such invasion of the animal, but, rather, by introducing a radioactive chelate of indium and an 8-hydroxyquinoline into the bloodstream of the animal. After a suitable period, the chelate accumulates not only in certain areas of the body such as the liver and spleen, but, also, in relatively large amounts in any inflamed area present. The body can then be subjected to a radio survey by an external imaging technique to detect the accumulated radioactivity in the location of an inflamed area providing the latter is in a part of the body other than one in which the chelate would normally accumulate to essentially the same extent even in the absence of inflammation. This procedure is relatively rapid and convenient, and avoids the use of external or in vitro tagging procedures which have heretofore been employed for similar purposes.

Radiopharmaceutical imaging is a widely practiced procedure for the purpose of making various types of determinations regarding the condition of the body of warmblooded animals. Not only are such procedures advantageous in the veterinary field and in facilitating research in various pharmaceutical areas, but, indeed, an area of wide application is in evaluating or examining the human body. The useful radiopharmaceuticals generally emit gamma photons that can be detected by external imaging to ascertain the location of the radioactive material in the body, but there are limitations in various imaging systems that may restrict the type of radioisotopes that can be employed, as well as the manner in which the procedure must be executed. The radioactive substance must be effective in relatively low dosages and have sufficient life and selectivity in depositing in the desired body area in order for the procedure to be successful.

With respect to body abscesses their presence and locations have heretofore been determined by labeling blood components in vitro, and then introducing the resulting materials into the body of the animal to be examined by radioassay. This process is highly disadvantageous in that the blood sample must be first withdrawn, the desired component of the blood separated and labelled and then reinjected into the animal in relatively large amounts before the procedures are generally successful. A process of this type is described in, for example, "INDIUM-111-LABELED AUTOLOGOUS LEUKOCYTES IN MAN", Mathew L. Thakur et al., *Journal of Nuclear Medicine*, Volume 18, No. 10, 1014–1021.

It has been disclosed in U.S. Pat. No. 4,017,596 that various radiometal diagnostic agents may be injected in warmblooded animals such as mice and dogs. These agents are described as having a high degree of in vivo stability and being highly specific to accumulation in certain organs or anatomical areas and exhibiting excellent nuclear imaging properties. Chelates of 8-hydroxyquinoline and indium-111 or indium-113m are said to be useful agents from the standpoint of in vivo stability and high activity, permitting their use in relatively small amounts. The patent, however, has no disclosure pertaining to the accumulation of radioactivity in the body of the animals due to the presence of inflammation caused by a diseased condition or other inflammatory reaction.

The present invention is based on the finding that radioactive indium chelates of an 8-hydroxyquinoline when provided in small, effective amounts in the bloodstream of a warmblooded animal having an inflammatory body reaction, accumulate in the inflamed area of the body to an extent sufficient for relatively ready detection by scanning or other suitable external radioassaying techniques providing such accumulation is significantly greater than would occur in the same part of the body in absence of the inflammation. The procedure of the invention can be used as a diagnostic tool not only in animals that are considered to have an inflammatory body reaction but, also, to ascertain whether or not inflammation even exists in the body in question. The present invention may be used to locate body abscesses or other inflammatory reactions in the body caused, for instance, by infections, organ transplants employing real or artificial organs, bone prothesis, the presence of other alien object in the body, or other injury.

In the process of the invention the chelates apparently serve to form in vivo, radioactive blood components in the bloodstream of the animal which components accumulate in body abscesses. Various mammals can be treated by this procedure including, for example, dogs, goats, humans, rodents, and the like. The indium chelates of an 8-hydroxyquinoline can be the indium-111 or indium-113m complexes described in U.S. Pat. No. 4,017,596, and, thus, may be 8-hydroxyquinoline in unsubstituted or substituted forms which have substantially equivalent complex constants and lipophilic properties. Such materials may enter the cell and the complex is broken to provide the desired effect. The substituted moiety of 8-hydroxyquinoline may be, for instance, one or more hydrocarbyl groups, for example, alkyl such as methyl or other lower alkyl groups, or other substituents. Of course, the chelate should not unduly adversely affect the body into which the agent is injected.

In the present invention the indium chelate can be injected into the bloodstream of the animal as by intravenous or subcutaneous administration, and the amount of imaging agent introduced may be quite small. Generally, the chelate can be introduced into the body in an amount up to about 0.036 millicurie of radioactivity per pound of body weight, and, preferably, this amount need not exceed about 0.0143 millicurie per pound. The amount should be sufficient so that the agent accumulated in the inflamed area can be effectively detected, for example, at least about 0.00036 millicurie, preferably at least about 0.0036 millicurie, per pound of body weight. The radioactive agent may be applied as a solution containing a small, effective amount of the chelate as oxine, for instance, about 0.005 to 0.2 milligram, preferably about 0.01 to 0.05 milligram, per milliliter of solution. The amount of solution injected into the bloodstream need not exceed more than a few milliliters, preferably being less than about 5 milliliters, and the amount need only be sufficient to enable the desired detection to be made subsequently, e.g., at least about 0.0036 milliliter per pound of body weight. Frequently, these amounts are about 0.007 to 0.014 milliliter of solution per pound of body weight. The solution may often have about 0.02 to 5 or 10 millicuries of radioactivity per milliliter of solution, preferably about 0.1 to 0.5 millicurie per milliliter.

After the radioactive imaging agent has been introduced into the body of the animal, the radioassay may be accomplished by utilizing various radioscanning techniques employing gamma ray detection such as by scintillation camera and the like. Generally, it has been found that the desired accumulation of radioactivity in the inflamed area occurs sufficiently for detection after about one hour or so and the life of the radioactive indium imaging agent is sufficiently extended to permit the scanning to be accomplished up to several days after injection into the body. At the same time, however, this life is not so extended that it poses an excessive radiation burden to the body.

In order to evaluate the process of the invention, it was compared with the known process which utilizes in vitro labeled leukocytes as an aid to the diagnosis and localization of abscesses. The inherent ability of leukocytes to accumulate rapidly and in large numbers at sites of acute inflammation makes them an ideal vehicle for the transport of a radioactive agent to, and therefore, the identification of, areas of inflammation. Indium-111 is an especially suitable isotope for scanning and gamma camera imaging, with a half-life (68 hours) which is long enough to enable scanning to be continued for up to about 3 to 4 days, yet not so long that it poses an excessive radiation burden. Indium will not itself label cells, but will when chelated to a lipophilic 8-hydroxyquinoline (oxine) molecule which transports it through the cell membrane and into the cell. The cell is then firmly labeled as the indium is unable to return through the cell membrane. In the work reported below the use of In-111-oxinate labeled autologous granulocytes is compared with the injection of plain In-111-oxinate and with plain In-111-chloride. Imaging was accomplished with a gamma ray camera, by tissue distribution studies and by clearance studies.

The use of the radioactive agents was also evaluated with respect to both sterile abscesses and bacterial abscesses. Sterile abscesses were evoked by injecting goats subcutaneously at multiple sites at the flanks with 3 ml of a 1:1 emulsion of phosphate-buffered, saline pH 7.2 (PBS) in mineral oil (Freund's complete adjuvant, Difco Laboratories, Detroit 1, Mich. U.S.A.). The injections were repeated at intervals. The animals developed firm abscesses with a diameter of 2 cm. The development of a solid abscess took at least one or two weeks. Although some of these abscesses produced pus; most of them did not, but attained a solid encapsulated state when they were a couple of months old. At the time of the abscess imaging one goat had abscesses of 0, 1, 2, 5, 7, 9, 12, 14 days and 7 months old.

Bacterial abscesses were also evoked in goats in accordance with the following procedure: 4 Droppings (faeces) of goats were stirred in 10 ml phosphate-buffered, saline solution (pH 7.2), emulsified in 10 ml mineral oil (Freund's complete adjuvant), and injected subcutaneously into four goats (2.5 ml per goat) at the left flank of the abdomen. Within a day the goats developed fever (temperature rose from 39.3° to over 40° C.) and a firm abscess with a diameter of about 10 cm. appeared. After three days the temperature of the animals was normal again and the abscesses became softer indicating that the goats were able to recover without any help.

In order to prepare granulocyte suspensions blood was sampled from a goat via the neck vein, and anticoagulated by the addition of heparin. The granulocytes were purified by a known sedimentation technique. The separation fluid consisted of: 10 Parts of Isopaque (sodium metrizoate) (32.8%) mixed with 24 parts Ficoll (Pharmacia) 8% (in $H_2O$). The density was: 1.077 g/ml. Equal parts of anticoagulated blood and 0.9% NaCl were mixed and 20 ml of the mixture was layered over 10 ml of Isopaque-Ficoll in a centrifuge tube. The mixture was centrifuged at 1000 g for 15 minutes. After centrifugation the mononuclear cells (monocytes and lymphocytes) were found as a narrow band at the interface between the plasma layer and the separation fluid. The layer above the erythrocyte sediment, also containing granulocytes, was removed down to 1 to 2 mm above the erythrocyte meniscus. The erythrocyte layer was mixed with a 3 to 5 fold volume of phosphate-buffered saline solution and centrifuged for 7 minutes at 1200 g. The supernatant was pipetted-off down to the erythrocyte meniscus. The erythrocytes were lysed by addition of 30 ml 155 mM $NH_4Cl$ solution (also containing 10 mM $KHCO_3$ 0.1 mM EDTA) pH 7.4, mixing and 15 minutes storage at 4° C. After centrifugation (400 g) the granulocytes were resuspended in $NH_4Cl$ solution (15 ml) 0.5% albumin and stored 15 minutes at 4° C. After microscopic control the cells were washed in PBS containing 0.5% albumin and were consecutively suspended in 5 ml PBS containing 0.5% albumin. In that condition the cells are ready for indium-111-oxinate labeling.

Indium-111-oxinate labeled granulocytes were made by the Thakur procedure. In this preparation 2×50 ml conical centrifuge tubes are sterilized at 120° C. for 2 hours. In-111 $Cl_3$ (Byk-Mallinckrodt CIL B.V.) 0.1 M HCl solution (5 mCi/ml) is used. 1 ml $H_2O$ is added for injection, as are 50 $\mu l$ oxine (BDH or Merck) solution (1 mg/ml in ethanol), and 200 $\mu l$ acetate buffer 0.3 M pH 5.6 after a short wait of about a minute. The In-111-oxinate is extracted into about 2 ml $CHCl_3$, and is evaporated to dryness by heating in a water bath. The material is dissolved in 100 $\mu l$ absolute ethanol and again evaporated and dissolved in 50 $\mu l$ absolute ethanol. 150 $\mu l$ saline is added after which cell-labeling proceeds immediately by adding 150 $\mu l$ In-111-oxinate to 5 ml of cells and incubate for 15 minutes at room temperature. The cells are intravenously administered to the test animal.

The measuring of the chemotactic activity can be considered as a useful parameter of the viability of white blood cells because in vivo the movement into gradients of foreign substances produced at sites of inflammation is a main physiological function of those cells. As a routine, isolated granulocytes ready to be labeled with In-111-oxinate were tested for chemotactic activity according to a known micropore filter technique. A millipore filter (3 $\mu m$) is fixed on top of a disposable tube which is dipped (with the filter down) into a beaker containing casein solution. The tube contains the granulocytes which will move in the direction of the casein through the pores of the filter. After 70 minutes incubation at 37° C. the filter is examined under the light microscope and the distance that the granulocytes moved into the filter is determined. A distance of 60–80 $\mu m$ is the standard distance which is covered by viable granulocytes.

The granulocyte suspensions used in the goat studies reported below consisted of viable cells as measured by their chemotactic response. It can be seen that the foregoing procedures relating to the separation of granulocytes, the determination of their viability and their labeling involve considerable work and expense that can be avoided by using the process of the present invention.

For scintigraphy the goats were sedated with 1.5 ml Vetranquil (Philips-Duphar B.V., Amsterdam, Holland) and kept in the proper position under the gamma ray camera after injection of the In-111-oxinate labeled autologous granulocytes or other isotope formulations. Pictures were taken at intervals post injection.

The distribution of In-111 was determined in the different organs and tissues of three goats. One goat was injected with In-111-oxinate labeled autologous granulocytes, one with plain In-111-oxinate and one with plain In-111-chloride. The injections with the isotope formulations took place 2 days before the animals were sacrificed and dissected. Pieces of abscess, organs and tissues were sampled, weighed and the radioactivity was measured in a scintillation counter. The radioactivities per gram of tissue were determined.

The clearance of In-111 from the blood of the goats was followed after intravenous injection of In-111 in three different formulations, namely In-111-chloride, In-111-oxinate and In-111-oxinate labeled granulocytes, respectively, in order to determine the biological half life for each of these different formulations. After injection, 10 ml blood samples were taken at intervals. All blood samples were subjected to differential centrifugation in order to determine whether the radioactivity was localized in the plasma, platelets, red cell fraction or leukocytes. Platelet rich plasma (PRP) was prepared by centrifugation of heparinised blood at 200 g during 15 minutes. After sampling of the PRP (1 ml) the residue was centrifuged at 1600 g for 10 minutes. 1 ml samples were taken from the plasma layer (platelet poor plasma=PPP), from the interface between plasma and red cells (leukocytes) and from the red cell fraction. The radioactivities were determined and clearance was determined corrected for physical decay.

After evoking the last sterile abscess the goat was bled and granulocytes were isolated, labeled with In-111-oxinate (ca. 1 mCi) and reinjected into the goat. The goat was imaged by scintigraphy the next day. At first there was the impression that a few 7 months old sterile abscesses seemed to yield positive spots on the gamma camera pictures, but comparison with a bone scintigraphy showed that one spot corresponded to the ileosacral region of the skeleton and the other to the bladder. The abscesses of 0, 1, 2, 5, 7, 9, 12 and 14 days all yielded negative pictures. The cause of this result may be the fact that sterile abscesses develop very slowly accompanied by a limited inflammation and a solid encapsulation, more resembling a cyst than an abscess. A strong uptake of activity was seen in the bones, the lungs and the liver.

Within two days after evoking the bacterial abscesses, one goat was bled and granulocytes were isolated by Ficoll-isopaque density centrifugation, labeled with In-111-oxinate (ca. 1 mCi) and reinjected into the goat. The goat was imaged by scintigraphy the next day. The abscess showed up as a clear spot.

A week later again two goats were injected with a faeces emulsion at the same site in the left flank of the abdomen. Next day the goats were bled, granulocytes were isolated, labeled and reinjected. The goats were imaged by gamma camera and here also the abscesses showed up as clear spots.

The tissue distribution of In-111 in the goat was determined to show the distribution of radioactivity among the organs. The goat was sacrificed and high radioactivity was found in the kidney. An inflamed lymph node had three times the radioactivity of a non-inflamed one. The abscess had a moderate radioactivity accumulation, more than blood and muscles; however, far less than, for example, the ovaria, uterus, lungs, kidneys and spleen. So only with the low local background of the flank of the abdomen was it possible to visualize the abscess. This result may, however, be due to the choice of animal used in the study. Heart muscle showed moderate accumulation of radioactivity compared to blood. The heart showed clear signs of bacterial pericarditis.

In order to illustrate the process of the invention a goat with adjoining bacterial abscesses of 2 months and three days old was injected with In-111-oxinate (ca. 1 mCi). The goat was imaged by gamma camera the next day. The abscess showed up as a clear spot on the photograph. The goat was sacrificed and the distribution of radioactivity between the different tissues and organs determined. There was a strong accumulation of In-111 in the cell fraction of the blood, almost as much as the radioactivity per gram of tissue of the spleen. An additional washing of the cells with PBS showed that the radioactivity was firmly bound. This was in contradiction to a goat which was injected with plain In-111-chloride. In the latter case only a small amount of In-111 accumulated in the blood cells which could be easily washed out. In the case of the In-111-oxinate injection an inflamed lymph node had two times the radioactivity of a non-inflamed one. Tissue of the new abscess had a moderate radioactivity accumulation more than, for example, the lymph node and muscles, but far less than ovarium, uterus, lung, kidney, spleen and blood. Tissue of the old abscess, however, had a high accumulation of In-111, similar to the kidney and ovarium. This was in correspondence with the clear spot on the gamma camera pictures. Pus of the old and new abscesses contained little radioactivity. This was similar to the situation in the goat injected with In-111-oxinate labeled granulocytes. The fat, muscle, marrow from the femur, gall, faeces, pancreas and urine showed no significant accumulation of radioactivity. Heart muscle showed a moderate accumulation of In-111.

A goat with bacterial abscesses of 2 months and three days old was injected with In-111-chloride (ca. 1 mCi). By accident the injection was not intravenously but subcutaneously. The radioactivity spread via the peripheral vascular system, not via the neck vein to the heart and the lungs. Nevertheless, twenty-four hours later the abdomen of the goat by gamma camera was imaged and the region of the abscess showed up as a distinct, well-visible spot.

The experiment with plain In-111-chloride was repeated in another goat with adjoining bacterial abscesses of 2 months and three days old. The injection was of about 1 mCi In-111-chloride and was accomplished intravenously. Gamma camera imaging the next day showed the region of the abscess as a well-visible spot.

The goat that was intravenously injected with In-111-chloride was dissected two days after the injection, and the distribution of radioactivity among the different tissues and organs determined. In contrast with the tissue distribution study with In-111-oxinate the blood was very moderately labeled. Most of the radioactivity was in the plasma, not in the cells. Besides the radioactivity in the cells could be washed out by PBS in contradistinction to the blood cells in the In-111-oxinate study. An inflamed lymph node had three times the radioactivity of a non-inflamed one. Tissue of old and new abscesses had moderate radioactivity, somewhat more than lymph node and muscle, far less than ovarium, uterus, lung and kidney. The abscess was also intraperitoneally penetrated. This part of the abscess showed a slightly higher accumulation of radioactivity, but the accumulation was less than in the old abscess in the In-111-oxinate study. Pus of the old and new abscesses contained hardly any radioactivity and conformed to the other distribution studies. There were moderate accumulations of radioactivity in the spleen and liver. The fat, urine and gall showed no significant accumulation of In-111. The kidney was, again, strongly labeled.

The clearance of In-111 from the blood of goats was followed after intravenous injection of In-111 in three different goats and formulations, namely, In-111-chloride, In-111-oxinate and In-111-oxinate labeled granulocytes, respectively, in order to determine the biological half-life of In-111. The clearance of indium after the In-111-chloride injection is shown by the decline to a very low level of radioactivity within two days and the indium almost disappeared in four days.

The clearance of In-111-oxinate in another goat showed a gradual increase of In-111 in the blood for two days. After that there was a very slow decline of the activity level. One week later there was still a significant amount of radioactivity in the blood. In this case there was a clear preference of In-111 to accumulate in the cell fraction of the blood. This accumulation is optimal five days after injection of the IN-111-oxinate. The ratio of the indium concentration in plasma and cells becomes 1:5, five days after injection.

In another experiment in another goat, a strong preference of the cells for indium-111-oxinate was found. The ratio of the agent in the plasma to red cells was 1:8.

There was no preference of indium-111 for white cells, however, the sample had about an equal amount of plasma. There was a gradual decrease of radioactivity immediately after the goat was injected.

The clearance of In-111 in a goat which was injected with In-111-oxinate labeled granulocytes was also studied. Almost all activity remained in the white cell fraction. The radioactivity in this fraction declined very gradually to a rather low level after one week. This experiment confirms that the labeled granulocytes stay in the circulation for several days and must be viable. Only a minor part of the radioactivity is lost by the granulocytes as the low plasma and red cell radioactivity levels clearly show. A biological half-life of about three days was indicated for the granulocytes.

I claim:

1. A method for radioassaying a warmblooded animal to locate an inflammatory reaction which comprises providing in the bloodstream of said animal a small amount of a radioactive indium-8-hydroxyquinoline sufficient to form indium-radioactive blood components in said animal for detection by external imaging, and subjecting said animal to external imaging for detecting accumulated radioactivity in an inflamed area to determine its location in the body of said animal.

2. A method of claim 1 in which said animal is a mammal.

3. A method of claim 1 or 2 in which said animal has a bacterial body abscess.

4. A method of claim 1 or 2 in which the radioactive material is indium-111-8-hydroxyquinoline.

5. A method of claim 4 in which said animal has a bacterial body abscess.

6. A method of claim 1 or 2 in which indium-111-8-hydroxyquinoline is administered to said animal as a solution containing about 0.02 to 10 millicuries of radioactivity per milliliter of solution.

7. A method of claim 6 in which said animal has a bacterial body abscess.

* * * * *